United States Patent

Speckman et al.

Patent Number: 5,338,291
Date of Patent: Aug. 16, 1994

[54] GLAUCOMA SHUNT AND METHOD FOR DRAINING AQUEOUS HUMOR

[75] Inventors: Lori C. Speckman, Ventura; David A. Watson, Goleta, both of Calif.

[73] Assignee: Pudenz-Schulte Medical Research Corporation, Goleta, Calif.

[21] Appl. No.: 12,995

[22] Filed: Feb. 3, 1993

[51] Int. Cl.⁵ .......................... A61F 2/14; A61M 5/00
[52] U.S. Cl. ............................................ 604/9; 623/4; 604/8
[58] Field of Search .................... 623/4; 604/8, 294, 9, 604/10, 8, 294; 606/108

[56] References Cited

U.S. PATENT DOCUMENTS

| | | | |
|---|---|---|---|
| 3,159,161 | 12/1964 | Ness | 623/4 X |
| 4,521,210 | 6/1985 | Wong | 604/8 |
| 4,722,724 | 2/1988 | Schocket | 604/8 |
| 4,729,761 | 3/1988 | White | 604/8 |
| 4,767,400 | 8/1988 | Miller et al. | 604/8 |
| 4,968,296 | 11/1990 | Ritch et al. | 604/8 |
| 5,171,213 | 12/1992 | Price | 604/9 |
| 5,178,604 | 1/1993 | Baerveldt et al. | 604/8 |

FOREIGN PATENT DOCUMENTS

| | | | |
|---|---|---|---|
| 9112037 | 8/1991 | PCT Int'l Appl. | 604/8 |
| 2187963 | 9/1987 | United Kingdom | 623/4 |

*Primary Examiner*—David H. Willse
*Attorney, Agent, or Firm*—Kelly, Bauersfeld & Lowry

[57] ABSTRACT

An implantable shunt device useful in treating glaucoma includes an episcleral plate and a catheter having a first end adapted for insertion into the anterior chamber of the eye, and a second end mounted adjacent to the episcleral plate. A slit valve is provided in a wall of the catheter between the first end and the second end, and the opposing, generally planar surfaces of the episcleral plate are textured to interrupt the formation of a dense fibrous capsule and to promote vascularization around the episcleral plate. In order to restrict the flow of fluid through the catheter to the episcleral plate until a fibrous capsule forms around the episcleral plate, the catheter is temporarily occluded utilizing a biodegradable ligation tied between the slit valve and the second end of the catheter. In the immediate post-operative period, excess aqueous humor is forced to flow through the slit valve, which provides a significant pressure drop. Once the ligature is resorbed, aqueous humor is free to flow through the catheter to the episcleral plate for resorption into the vascular system.

20 Claims, 2 Drawing Sheets

GLAUCOMA SHUNT AND METHOD FOR DRAINING AQUEOUS HUMOR

BACKGROUND OF THE INVENTION

This invention relates generally to the drainage of aqueous humor from an eye to relieve the elevated eye pressure characteristic of glaucoma. More specifically, the present invention relates to an implantable glaucoma shunt device and related method, which prevents excess drainage of aqueous humor during the early post-operative period, and yet permits sufficient fluid flow from the eye during long term use.

Aqueous humor is continuously produced by the ciliary body in the posterior chamber of the eye, and from there it flows into the anterior chamber. In order to maintain relatively constant intraocular pressure, aqueous humor must be drained away continuously. It passes through the trabecular meshwork and into the canal of Schlemm, before draining into the veins leaving the eye.

Normal intraocular pressure typically ranges from about 15±3 mm Hg., but may be up to 21 mm Hg. Pressures substantially above this range are considered abnormally high. Chronically elevated intraocular pressure (resulting, for example, from a defect in intraocular drainage) can give rise to glaucoma. Glaucoma can cause irreversible damage to certain structures of the eye, including the retina, and is the leading cause of blindness in the United States.

There are many types and causes of glaucoma. Optimal treatment depends on the patient's form of glaucoma. As a rule, the damage caused by glaucoma cannot be reversed. The goal, therefore, of treatment is to prevent further damage and to preserve existing vision.

Glaucoma can often be controlled with medical therapy, typically through topical medications (eyedrops) and systemic medications (pills). Medical therapy either decreases the rate of formation of aqueous humor, or increases its outflow from the anterior chamber. Potential problems with medical treatment include side effects, inadequate control of the intraocular pressure, and poor patient compliance.

If the maximum-tolerated dose of medication fails to control the intraocular pressure, then laser trabeculoplasty or filtering surgery is usually indicated. These procedures seek to increase the rate of outflow of aqueous humor. Another type of surgical procedure seeks to reduce the rate of formation of aqueous humor, by destroying the tissue where it is created. These cyclodestructive procedures are typically indicated only after filtering surgery has failed. If such filtering surgery has failed to control the intraocular pressure, or if the patient has a poor prognosis for filtering surgery, implantation of a glaucoma shunt may be indicated.

Glaucoma shunts typically drain aqueous humor from the anterior chamber of the eye to a fibrous capsule (bleb) which forms around a collecting device placed on the posterior portion of the globe of the eye. Aqueous humor is then resorbed into the vascular system. Glaucoma shunts typically consist of a silicone elastomer catheter which is inserted into the anterior chamber, and which connects to an episcleral plate or an encircling band. Episcleral plates are commonly made of silicone elastomer, polypropylene or acrylic materials.

Glaucoma shunt surgery is subject to a number of common complications. In the early post-operative period, excess drainage of aqueous humor from the anterior chamber can cause low intraocular pressure and shallow anterior chamber depth. This can lead to choroidal detachment or hemorrhage. The low intraocular pressure is typically alleviated as the fibrous capsule forms around the posterior plate or encircling band. In the long-term, excess fibrosis of the capsule obstructs the flow of aqueous humor from the bleb into the vascular system. This causes an increase in the intraocular pressure, and results in clinical failure of the device.

Accordingly, there has been a need for a novel glaucoma shunt which, in the immediate post-operative period, can provide resistance to flow to maintain a desired intraocular pressure. Such a shunt should also interrupt the formation of a dense capsule around the shunt to ensure the continued resorption of aqueous humor by the vascular system, and help prevent long-term intraocular pressure elevation. Further a glaucoma shunt is needed which accomplishes the desired function and is easy to manufacture and use, and which provides the desirable shunting functions reliably over an extended period of time. The present invention fulfills these needs and provides other related advantages.

SUMMARY OF THE INVENTION

The present invention resides in an improved glaucoma shunt and in a method for draining aqueous humor from the eye. More specifically, the method for treating glaucoma with a surgically implantable device includes the steps of inserting a first end of a catheter into the anterior chamber of the eye, securing a plate connected to a second end of the catheter to the sclera of the eye, restricting the flow of fluid through the catheter to the plate and non-surgically removing, gradually over an extended length of time, the restriction on the flow of fluid through the catheter to the plate after a fibrous capsule forms around the plate. A slit valve is provided in a wall of the catheter between the first end and the second end, and the catheter is ligated between the slit valve and the second end in order to temporarily occlude the second end of the catheter during the immediate post-operative period and force excess aqueous humor to flow through the slit valve. Following implantation of the glaucoma shunt, the formation of a dense fibrous capsule around the plate is interrupted which, it is believed, promotes vascularization around the plate. The ligature utilized to occlude the catheter is biodegradable and once it is resorbed, there will be a free flow of aqueous humor from the anterior chamber of the eye to the plate whereat the excess aqueous humor will be resorbed into the vascular system.

In a preferred form of the invention the surgically implantable device comprises an episcleral plate, and a catheter having a first end adapted for insertion into the anterior chamber of the eye, and a second end mounted adjacent to the episcleral plate. The implantable device further comprises means for interrupting the formation of a dense fibrous capsule around the episcleral plate. The episcleral plate has a spherical arch-shape to match the shape of a posterior portion the eye, and means are provided for attaching the episcleral plate to the sclera. In order to interrupt the formation of the fibrous capsule and to promote vascularization around the episcleral plate, the opposing generally planar surfaces of the plate are textured. Each textured surface comprises a plurality of fingers extending generally uniformly outwardly from the episcleral plate. The fingers are spaced along the surface approximately 0.018 inch center to center from one another, and have dimensions of approximately 0.010 inch in width and approximately 0.011 inch in height.

A slit valve is provided in a wall of the catheter and is situated between the first end and the second end. Graphite is applied to the opposing faces of the slit valve to prevent adhesion between said opposing faces. The implantable shunt device further includes means for restricting the flow of fluid through the catheter to the episcleral plate until a fibrous capsule forms around the episcleral plate. Such restricting means comprises a biodegradable ligature between the slit valve and the second end of the catheter.

In the immediate post-operative period, the slit valve provides resistance to the flow of aqueous humor from the eye in order to maintain a sufficient intraocular pressure. The ligature between the slit valve and the second end of the catheter occludes the catheter to force all fluid flow through the slit valve, providing a significant pressure drop. Once the ligature is resorbed there is a free flow of aqueous humor from the anterior chamber through the catheter to the episcleral plate. Aqueous humor is there resorbed into the body through the fibrous capsule which formed around the episcleral plate. The implantable shunt device of the present invention thus prevents excess drainage of aqueous humor from the anterior chamber in the early post-operative period during the formation of the fibrous capsule about the episcleral plate. Excess fibrosis of the capsule, which may undesirably obstruct the flow of aqueous humor from the capsule into the vascular system following resorbtion of the ligature, is prevented by texturing the episcleral plate. Such texturing interrupts the formation of a dense fibrous capsule and promotes vascularization around the episcleral plate.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
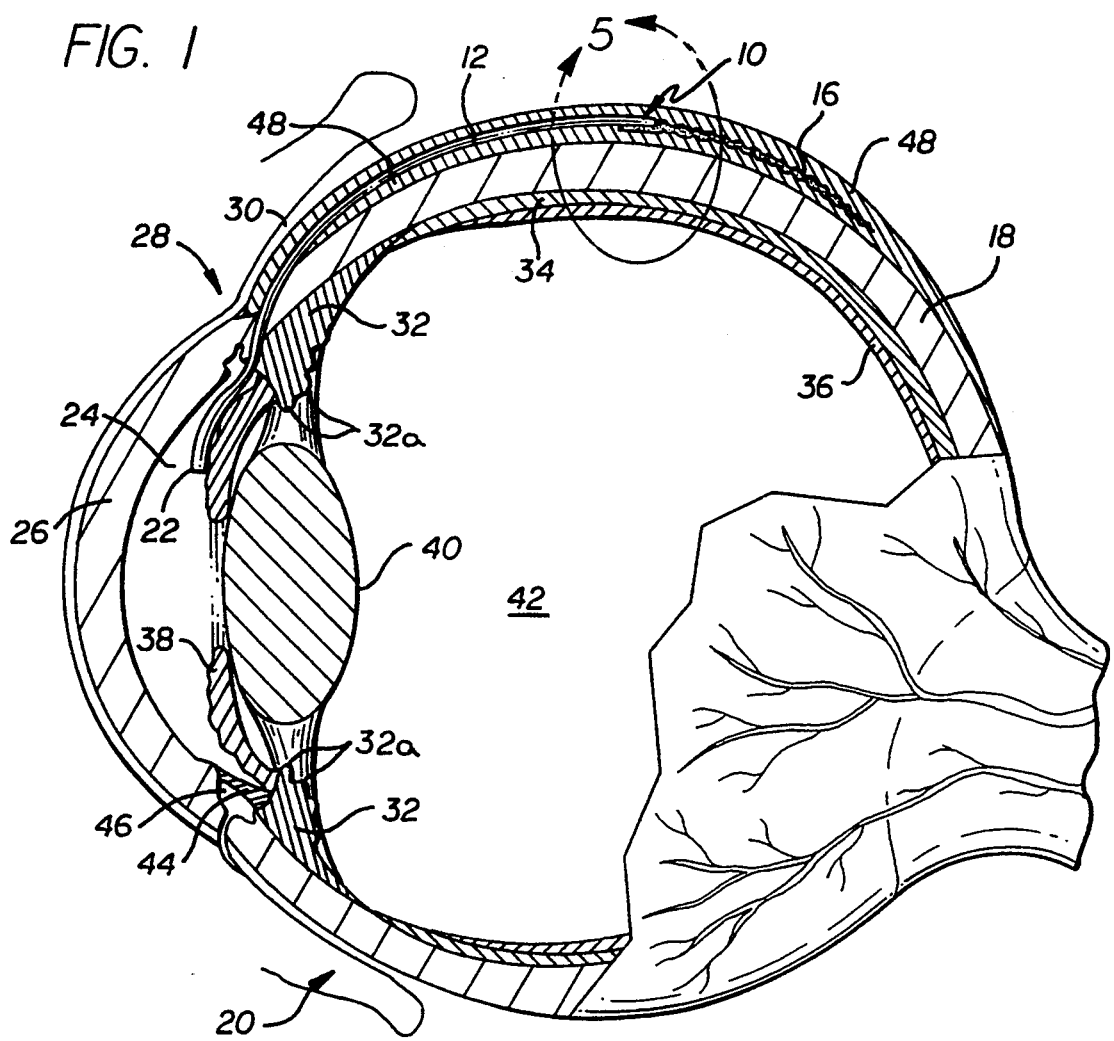
FIG. 1 is an elevational and partially sectional view of an eye, illustrating a glaucoma shunt embodying the present invention extending from the anterior chamber of the eye to the posterior portion of the globe of the eye wherein is situated an episcleral plate surrounded by a fibrous capsule (bleb)

As shown in the drawings for purpose of illustration, the present invention is concerned with an improved glaucoma shunt device, generally designated by the reference number 10. The improved glaucoma shunt device 10 comprises a catheter 12 which is attached at a second end 14 thereof to an episcleral plate 16. The shunt device 10 is implanted during a surgical procedure wherein the episcleral plate 16 is placed adjacent to a posterior portion of the sclera 18 of an eye 20, and a first end 22 of the catheter 12 extends into the anterior chamber 24 of the eye.

With reference to FIG. 1, the eye 20 will be explained generally to facilitate an understanding of the present invention. As shown, a transparent cornea 26 at the front of the eye 20 merges into a generally spheroidal sclera 18 at an annular junction designated as the limbus 28. The conjunctiva 30 extends posteriorly from the limbus 28 over the front half of the eye and then projects in a forward direction, underlying the upper and lower eyelids. In apposition with the interior side of the sclera 18, and beginning at the limbus 28, the ciliary body 32 extends posteriorly until it becomes the choroid 34, a layer containing many blood vessels. The choroid 34 extends further rearwardly around the back of the interior of the eye 20, and in turn is covered on its interior surface with the retina 36.

Near the forward end of the ciliary body 32, the diaphragm-like iris 38 extends radially inwardly of the eye 20 to provide automatic control of the amount of light reaching the lens 40, which is positioned just behind the iris. The central portion of the eye forward of the lens 40 contains the so-called aqueous humor, which is a rather thin watery eye fluid. The central portion of the eye rearward of the lens 40 is designated as the vitreous cavity 42, while the portion forward of the iris is designated as the anterior chamber 24.

The aqueous humor is generated primarily by the ciliary body 32, and specifically by the ciliary processes 32a rearward of the iris 38, and reaches the anterior chamber 24 through the pupil. In order to maintain relatively constant intraocular pressure, the aqueous humor must be drained away continuously. It passes through the trabecular meshwork 44, and into the canal of Schlemm 46, before draining into the veins leaving the eye 20.

In accordance with the present invention, and again referring primarily to FIG. 1, the glaucoma shunt device 10 is surgically implanted relative to the eye 20 to drain aqueous humor from the anterior chamber 24 to a fibrous capsule or bleb 48 which forms around the episcleral plate 16 placed on the posterior portion of the globe of the eye. Aqueous humor is there resorbed into the vascular system. The glaucoma shunt device 10 of the present invention is designed to solve problems encountered in the early post-operative period, as well as those found during long term usage of similar shunts. In particular, the shunt device 10 and a related method for treating glaucoma prevents excess drainage of aqueous humor from the anterior chamber 24 which can cause low intraocular pressure. Further, in the long term, excess fibrosis of the bleb 48 is minimized which could obstruct the flow of aqueous humor from the bleb into the vascular system.

Figure 2:
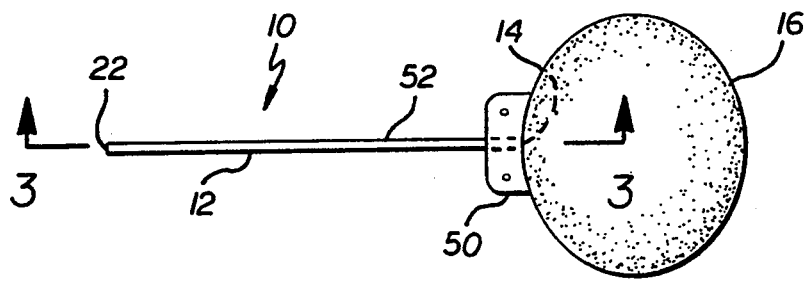
FIG. 2 is a top plan view of the glaucoma shunt illustrated in FIG. 1.
Figure 3:
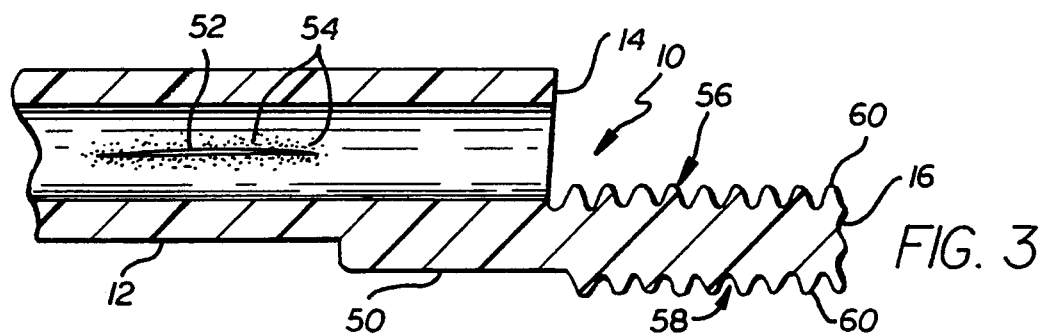
FIG. 3 is an enlarged fragmented sectional view of a portion of the glaucoma shunt taken generally along the line 3—3 in FIG. 2, illustrating a slit valve in a wall of a catheter adjacent to a second end thereof, the manner in which the catheter is attached to the episcleral plate, and surface texturing on the episcleral plate intended to interrupt the formation of a dense fibrous capsule and to promote vascularization around the episcleral plate.

Referring now to FIGS. 1-3, the catheter 12 includes the first end 22 which is adapted for insertion into the anterior chamber 24 of the eye 20, and the second end 14 which is mounted adjacent to the episcleral plate 16. The catheter 12 forms a fluid conduit for directing excess aqueous humor from the anterior chamber 24 to the episcleral plate 16, for resorption into the vascular system through the bleb 48 which forms around the episcleral plate after implantation. The catheter 12 may be attached to the episcleral plate 16 in any suitable manner, such as by bonding the components to one another. The catheter 12 and the episcleral plate 16 typically consist of a silicone elastomer material, but may be constructed of other suitable materials, possibly such as thermoplastic elastomer, polypropylene or acrylic materials. The episcleral plate 16 is molded to have a spherical arch-shape to match the shape of a posterior portion of the eye 20. The plate also includes an attachment flange 50 which a surgeon may suture directly to the underlying sclera 18 for secure placement of the plate 16 during the surgical procedure.

A slit valve 52 is provided in a wall of the catheter 12 adjacent to the second end 14. Graphite 54 is applied to the opposing faces of the slit valve 52 to prevent adhesion between the opposing faces.

In order to interrupt the formation of too dense a fibrous capsule or bleb 48 around the episcleral plate 16, and further to promote vascularization around the episcleral plate, the opposing primary, generally planar upper and lower surfaces 56, 58 of the episcleral plate 16 are textured. It is known that the surface finish of an implant influences local tissue reaction. Different histologic reactions to smooth and textured implants have been documented. Smooth-surfaced implants produce continuous, dense, organized capsules with fibers aligned parallel to the implant surface. Textured surfaces cause an interruption of this capsule formation, with multi-planar collagen deposition. See, for example, U.S. Pat. No. 4,955,909.

The textured upper and lower surfaces 56, 58 of the episcleral plate 16 comprise a plurality of fingers 60 extending outwardly from the episcleral plate. The fingers are spaced along each surface approximately 0.018 inch center to center from one another, and have dimensions of approximately 0.010 inch in width and approximately 0.010–0.012 inch in height. Such texturing of the surfaces 56 and 58 of the episcleral plate 16 of the glaucoma shunt device 10 acts to interrupt the formation of a dense capsule around the plate. This allows aqueous humor to continue to be resorbed by the vascular system through the bleb 48 and helps prevent long-term intraocular pressure elevation.

Figure 4:
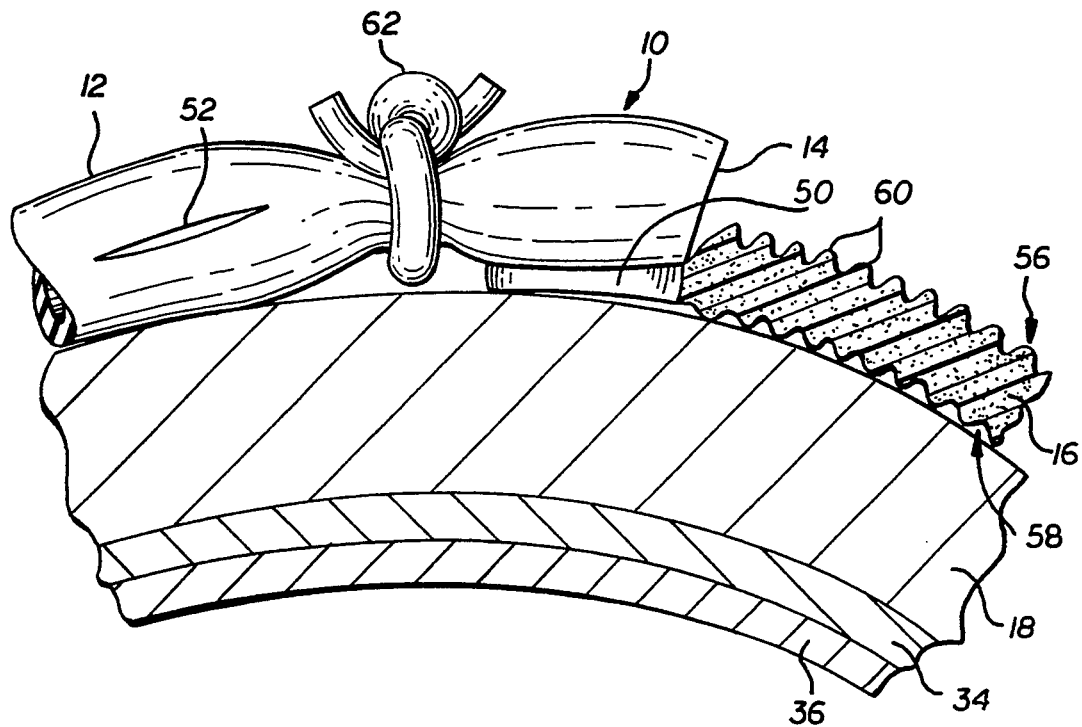
FIG. 4 is an enlarged fragmented elevational and partially sectional view of the glaucoma shunt and adjacent portion of the eye generally illustrated by the arrow 5 in FIG. 1, showing the manner in which a portion of the catheter between the slit valve and the second end is occluded utilizing a biodegradable ligature.
Figure 5:
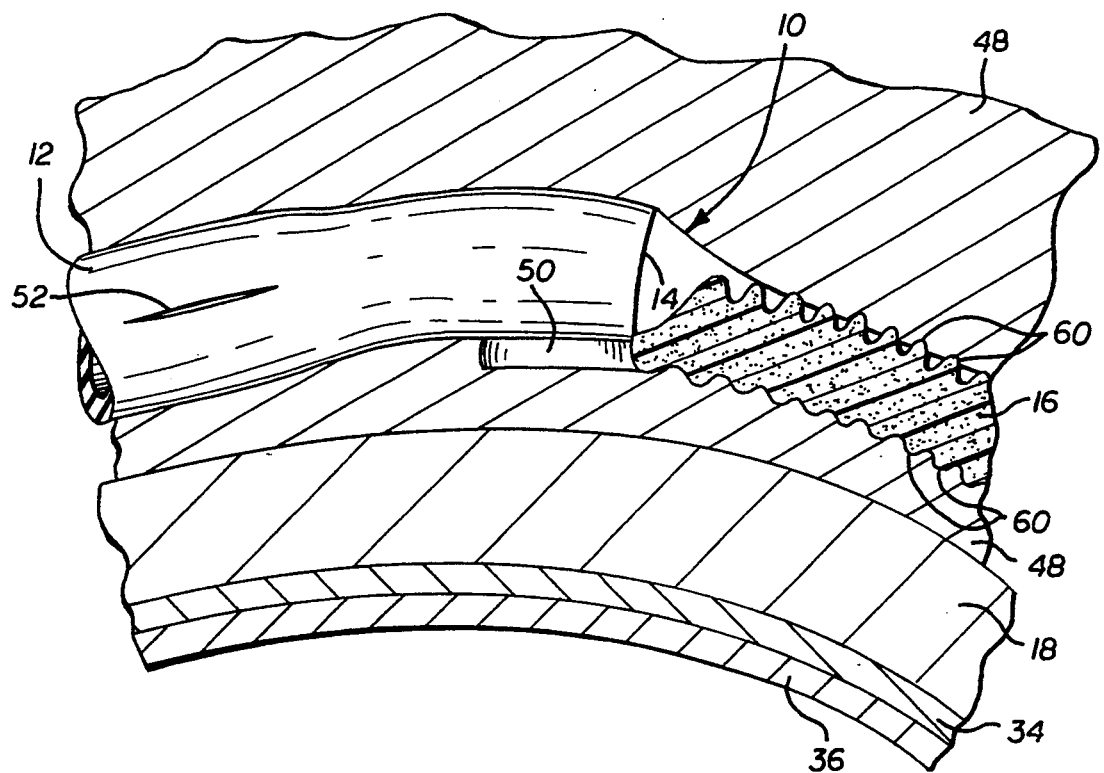
FIG. 5 is an enlarged fragmented elevational and partially sectional view of the glaucoma shunt and adjacent portion of the eye illustrated by the arrow 5 in FIG. 1, showing the configuration of the second end of the catheter, the slit valve and the adjacent portion of the episcleral plate after the ligature has been resorbed and a fibrous capsule or bleb has formed around the shunt.

With reference to FIG. 4, in order to prevent excess drainage of aqueous humor from the anterior chamber 24 in the early post-operative period, the flow of fluid through the catheter 12 to the episcleral plate 16 is restricted until the bleb 48 forms around the episcleral plate. To accomplish this, a biodegradable ligature 62 is tied about a portion of the catheter 12 between the slit valve 52 and the second end 14 of the catheter, in order to prevent fluid flow through the second end. With the ligature 62 in place, excess aqueous humor entering into the glaucoma shunt device 10 is only permitted to escape through the slit valve 52, which is structured to provide a significant pressure drop between fluid within the anterior chamber 24 and the surrounding biological environment. During the period in which the ligature 62 is being slowly resorbed into the body, the fibrous capsule or bleb 48 is forming about the second end 14 of the catheter 12 and the episcleral plate 16. This process takes approximately two weeks. Once the ligature 62 is resorbed, there will be a free flow of aqueous humor from the anterior chamber 24 to the posterior bleb 48 surrounding the episcleral plate 16, and the slit valve 52 will essentially close because it will offer a greater resistance to fluid flow than for fluid passing through the second end 14 of the catheter 12. Accordingly, the slit valve 52 does not contribute to undesirable long-term intraocular pressure elevation.

From the foregoing it is to be appreciated that the glaucoma shunt device 10 of the present invention can be implanted during a one-stage procedure, utilizes a permanent valve, and has an episcleral plate 16 having textured upper and lower surfaces 56, 58 which encourage development of a desirably less dense fibrous capsule or bleb 48 around the episcleral plate in comparison with prior glaucoma shunt devices. Additionally, the glaucoma shunt device 10 prevents excess drainage of aqueous humor from the anterior chamber 24 during the early post-operative period, and yet improves the long-term characteristics of the shunt device by changing the characteristics of the bleb 48 which forms around the episcleral plate 16.

Although a particular embodiment of the invention has been described in detail for purposes of illustration, various modifications may be made without departing from the spirit and scope of the invention. Accordingly, the invention is not to be limited, except as by the appended claims.

We claim:

1. An implantable shunt device useful in treating glaucoma, comprising:
   an episcleral plate having first and second surfaces, wherein at least one of the first and second surfaces includes texture means over substantially the entire surface thereof, for preventing excess fibrosis of a fibrous capsule forming around the episcleral plate;
   a catheter having a first end adapted for insertion into the anterior chamber of the eye, and a second end mounted adjacent to the episcleral plate; and
   a valve in a wall of the catheter, between the first end and the second end of the catheter to shunt fluid within the catheter to a location exterior of the catheter.

2. A shunt device as set forth in claim 1, wherein the texture means comprises a plurality of fingers extending outwardly from the episcleral plate, the fingers being spaced along the surface approximately 0.018 inch center to center from one another, and having dimensions of approximately 0.010 inch in width and approximately 0.011 inch in height.

3. A shunt device as set forth in claim 1, wherein the episcleral plate has a spherical arch-shape to match the shape of a posterior portion of the eye.

4. A shunt device as set forth in claim 1, including means for attaching the episcleral plate to the sclera.

5. A shunt device as set forth in claim 1, wherein the valve comprises a slit valve.

6. (Amended) A shunt device as set forth in claim 5, including graphite applied to opposing faces of the slit valve.

7. A shunt device as set forth in claim 1, including means for restricting the flow of fluid through the catheter to the episcleral plate until the fibrous capsule forms around the episcleral pate.

8. A shunt device as set forth in claim 7, wherein the restricting means comprises a biodegradable ligature between the valve and the second end of the catheter.

9. An implantable shunt device useful in treating glaucoma, comprising:
   an episcleral plate;
   a single-lumen catheter having a first end adapted for insertion into the anterior chamber of the eye, and a second end mounted adjacent to the episcleral plate;
   a valve in a wall of the catheter, situated between the first end and the second end of the catheter, for shunting fluid from the catheter lumen exteriorly of the catheter; and
   means for restricting the flow of fluid through the catheter to the episcleral plate until a fibrous capsule forms around the episcleral plate.

10. A shunt device as set forth in claim 9, including means for interrupting the formation of a dense fibrous capsule around the episcleral plate, the interrupting means including a first textured surface on the episcleral plate and a second textured surface on the episcleral plate, wherein the first and second surfaces each comprise a plurality of fingers extending outwardly from the episcleral plate.

11. A shunt device as set forth in claim 9, including means for attaching the episcleral plate to the sclera, and wherein the episcleral plate has a spherical arch-shape to match the shape of a posterior portion of the eye.

12. A shunt device as set forth in claim 9, wherein the valve comprises a slit valve and includes means for preventing adhesion between opposing faces of the slit valve, the adhesion preventing means including graphite applied to the opposing faces of the slit valve.

13. A shunt device as set forth in claim 9, wherein the restricting means comprises a biodegradable ligature between the valve and the second end of the catheter.

14. A shunt device as set forth in claim 9, wherein the episcleral plate includes first and second surfaces, and wherein at least one of the first and second surfaces includes texture means for preventing excess fibrosis of a fibrous capsule forming around the episcleral plate.

15. A shunt device as set forth in claim 14, wherein the texture means extends over substantially over the entire surface area of the at least one of the first and second surfaces.

16. A shunt device as set forth in claim 14, wherein the texture means comprises a plurality of fingers extending outwardly from the episcleral plate, the fingers being spaced along the surface approximately 0.018 inch center to center from one another, and having dimensions of approximately 0.010 inch in width and approximately 0.011 inch in height.

17. A method for treating glaucoma with a surgically implantable device, the steps comprising:
   inserting a first end of a catheter into the anterior chamber of the eye;
   securing a plate, connected to a second end of the catheter, to the sclera of the eye;
   providing a slit valve in a wall of the catheter between the first end and the second end thereof;
   restricting the flow of fluid through the catheter to the plate upon implantation of the surgically implantable device by ligating the catheter between the slit valve and the second end of the catheter; and
   non-surgically removing, gradually over an extended length of time, the restriction on the flow of fluid through the catheter to the plate after a fibrous capsule forms around the plate.

18. A method as set forth in claim 17, including the step of dissolving the ligation after a fibrous capsule forms around the plate.

19. A method as set forth in claim 17, including the steps of interrupting the formation of a dense fibrous capsule and promoting vascularization around the plate.

20. A method as set forth in claim 19, wherein the interrupting step includes the step of providing a non-planar surface texture to the plate.

* * * * *